US010653878B2

(12) United States Patent
Löfving et al.

(10) Patent No.: US 10,653,878 B2
(45) Date of Patent: May 19, 2020

(54) METHODS AND APPARATUS FOR STERILE CONNECTIONS

(71) Applicant: METENOVA AB, Mölndal (SE)

(72) Inventors: Alf Löfving, Torslanda (SE); Håkan Samuelsson, Onsala (SE); Lennart Myhrberg, Älvängen (SE); Sten Johansson, Göteborg (SE)

(73) Assignee: Metanova, AB, Mölndal (SE)

( * ) Notice: Subject to any disclaimer, the term of this patent is extended or adjusted under 35 U.S.C. 154(b) by 241 days.

(21) Appl. No.: 15/542,280

(22) PCT Filed: Jan. 8, 2016

(86) PCT No.: PCT/EP2016/050266
§ 371 (c)(1),
(2) Date: Jul. 7, 2017

(87) PCT Pub. No.: WO2016/110563
PCT Pub. Date: Jul. 14, 2016

(65) Prior Publication Data
US 2018/0264251 A1 Sep. 20, 2018

Related U.S. Application Data

(60) Provisional application No. 62/100,955, filed on Jan. 8, 2015.

(51) Int. Cl.
*F16L 23/12* (2006.01)
*A61M 39/18* (2006.01)
(Continued)

(52) U.S. Cl.
CPC ............ *A61M 39/18* (2013.01); *A61M 39/14* (2013.01); *F16L 23/12* (2013.01); *F16L 47/14* (2013.01); *F16L 2201/44* (2013.01)

(58) Field of Classification Search
CPC ....... F16L 2201/44; F16L 47/14; F16L 23/12; A61M 39/18; A61M 39/14
See application file for complete search history.

(56) References Cited

U.S. PATENT DOCUMENTS 3,909,910 A * 10/1975 Rowe .................... A61M 39/14
137/15.09
4,397,442 A * 8/1983 Larkin .................. A61M 39/14
137/68.29
(Continued)

FOREIGN PATENT DOCUMENTS

DE    102013214068 A1 *  1/2015 ............ A61M 39/18
EP         3225895 A1 * 10/2017 ............ A61M 39/18
(Continued)

OTHER PUBLICATIONS

International Preliminary Report on Patentability for PCT/EP2016/050266, dated Jul. 11, 2017, Authorized officer: Nora Linder.*
(Continued)

*Primary Examiner* — Anna M Momper
*Assistant Examiner* — James A Linford
(74) *Attorney, Agent, or Firm* — Finnegan, Henderson, Farabow, Garrett & Dunner LLP

(57) ABSTRACT

An apparatus or method for forming a sterile connection. The apparatus includes at least two sterile tubes each disposed within a flange. Each flange has an external face that completely covers the mouth of the tube. Each flange is designed to be displaced when force is applied to the tube to move the tubes toward one another such that the external face of each flange is displaced radially or axially outwards away from the mouth of the tube. When the external faces are displaced, the external face of each flange opens and tubes connect and form a sterile connection therebetween.

1 Claim, 8 Drawing Sheets

SECTION B-B    SECTION A-A

(51) Int. Cl.
*F16L 47/14* (2006.01)
*A61M 39/14* (2006.01)

(56) References Cited

U.S. PATENT DOCUMENTS

2008/0000833 A1  1/2008  Corbin et al.
2009/0232586 A1  9/2009  Diodati et al.

FOREIGN PATENT DOCUMENTS

| GB | 2 060 399 | 5/1981 | | |
|----|-----------|--------|---|---|
| WO | WO-2013147688 A1 | * | 10/2013 | ............ A61M 39/18 |
| WO | WO-2015069176 A1 | * | 5/2015 | ............ A61M 39/18 |

OTHER PUBLICATIONS

International Search Report from the European Patent Office for International Application No. PCT/EP2016/050266, dated Mar. 21, 2016.
Written Opinion of the International Searching Authority from the European Patent Office for International Application No. PCT/EP2016/050266, dated Mar. 21, 2016.

\* cited by examiner

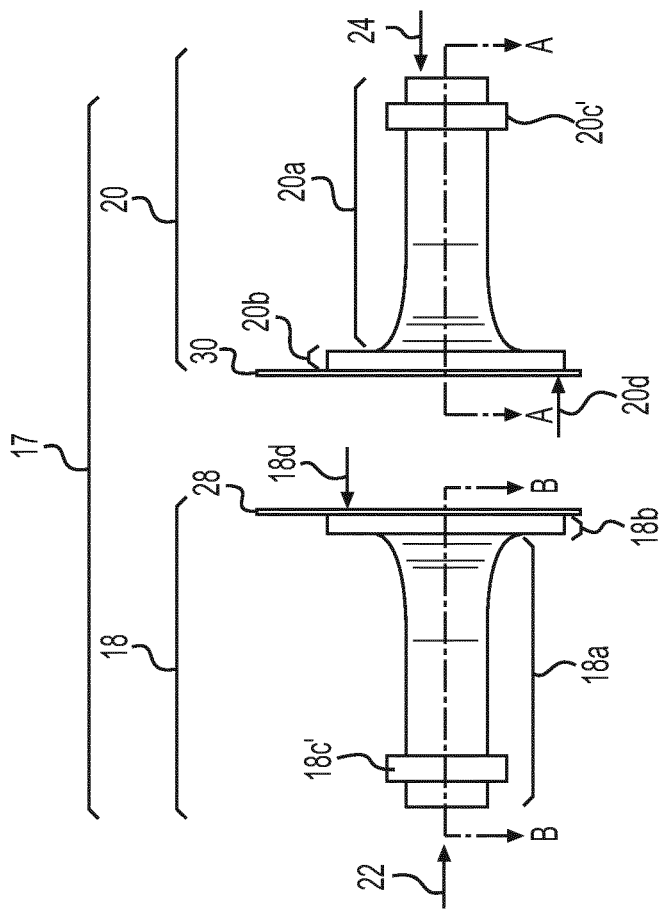
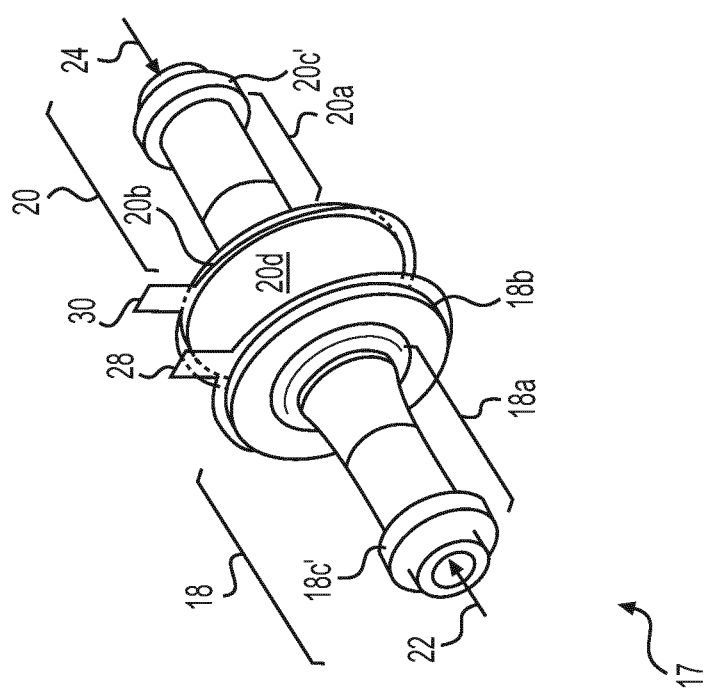
FIG. 2B
FIG. 2A

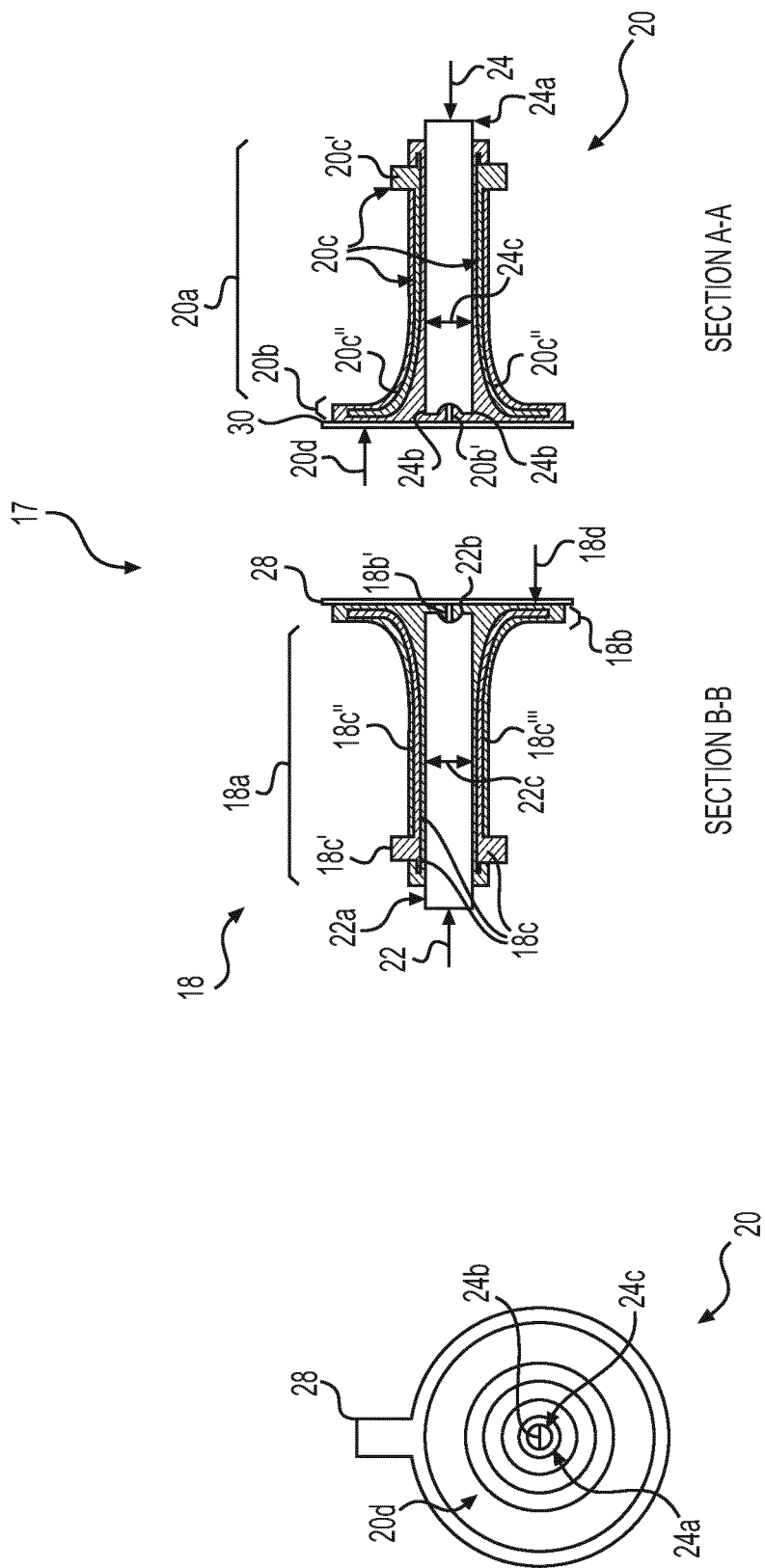

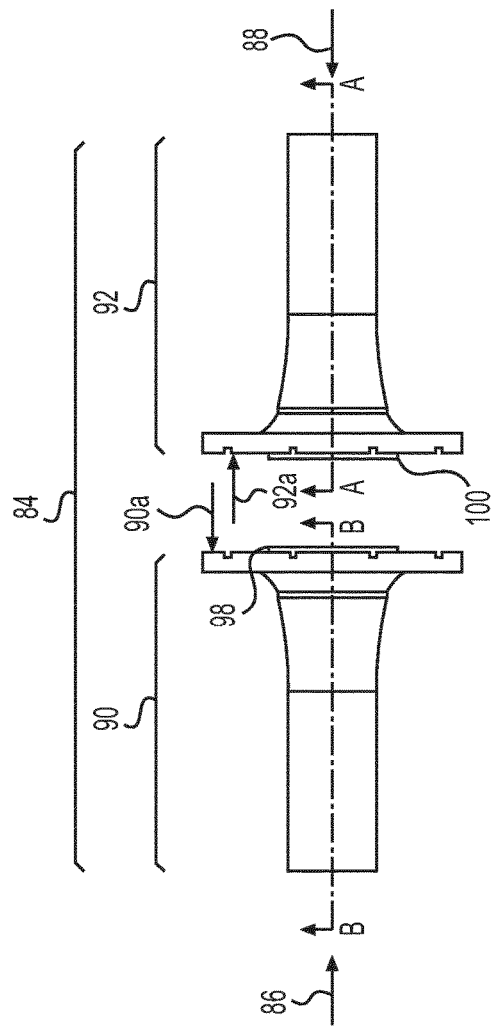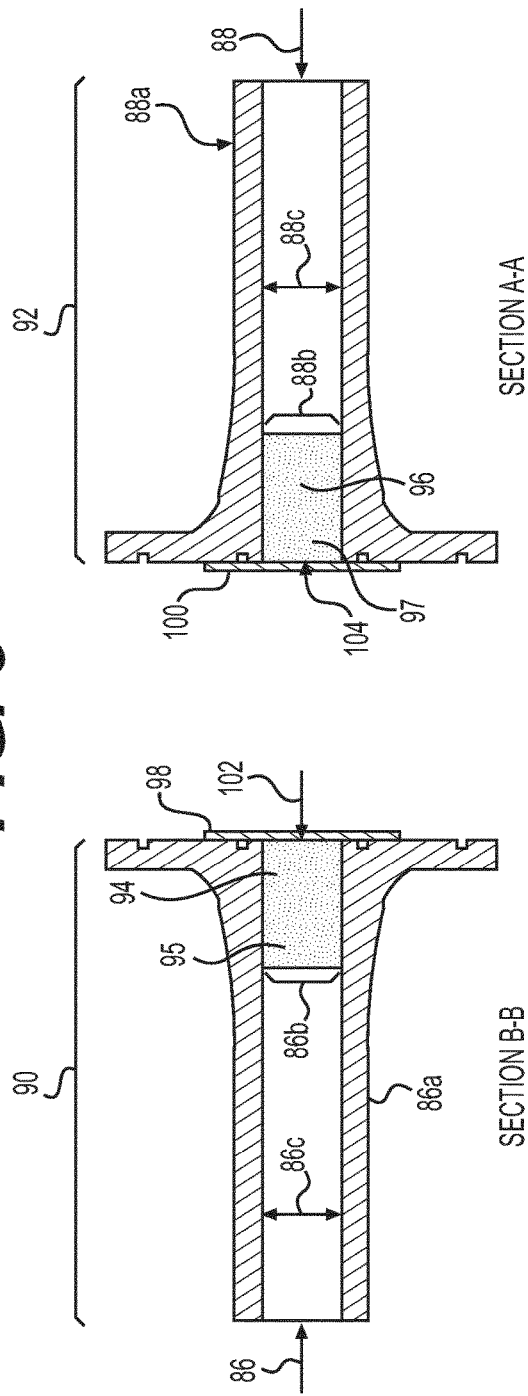

METHODS AND APPARATUS FOR STERILE CONNECTIONS

TECHNICAL FIELD

The present disclosure generally relates to methods and apparatus for creating a sterile connection between two or more product reservoirs, pieces of manufacturing equipment, processing tools, or the like.

BACKGROUND

Many industries endeavor to manufacture their products under sterile process conditions. For some industries, sterile processing is desirable, for other industries it is necessity. Pharmaceuticals, biotechnical products, food, and even cosmetics are often manufactured in sterile environments to avoid contamination.

Manufacturing such products often requires connecting different processing units together. For example, reservoirs and storage vessels are connected to mixing and processing devices. Finished batches are transported to production equipment. New ingredients are added, and the batches are tested during manufacturing. Each time one component is connected to another, exposure to airborne bacteria and/or other contaminants at the connection points jeopardizes the sterility of the entire system. This may result in decreased quality and potentially unsafe or unusable products.

Typical sterile connection techniques may present disadvantages. One option is to transform an entire processing facility or zone into a clean room. This is expensive. Another option is to steam-sterilize every connection. This is time-consuming, and limits the types of materials available for the equipment and connections. Another option includes covering each connection point with a sterile membrane. The connections are placed together and the coverings are removed simultaneously in an attempt to simultaneously uncover a sterile connection. But as the membranes are removed, a non-sterile surface or edge may cross through the sterile boundary, exposing the connection and the system to debris and bacteria.

The present disclosure is directed at a method and apparatus designed to overcome these and other shortcomings.

SUMMARY OF THE DISCLOSURE

One aspect of the present disclosure is an apparatus for creating a sterile connection between two or more sterile units. The apparatus comprises two flanges, each surrounding, forming, or connected to the distal end of a tube or other type of closed conduit, e.g., piping, suitable for transporting material from one unit to another. The tube or conduit may be of any size, shape, or material. The tubes have interior pathways that are sterile and are connected to other sterile units, e.g., reservoirs or other equipment. The two flanges are composed of a flexible material with a non-sterile external surface. A portion of each flange's external surface, forming an external face, covers the mouth of one of the sterile tubes. The external faces may be exposed to an external, non-sterile environment. The external faces are placed together, and attached permanently or temporarily using hook and loop, screws, snaps, welds, clamps, adhesive, magnetic force, pressure, mechanical fasteners and/or other attachment techniques suitable for substantially maintaining the connection between the external faces.

After the external faces are attached, the tubes, and portions of the flanges generally aligned with the tubes, are urged toward one another. The opposing forces cause the flexible material of the flanges to be radially and/or axially displaced relative to the axis of the tubes. The tubes move toward one another. As the external faces of the flanges are displaced, the interiors of the tubes are gradually exposed. First at a single point. Then the point expands as the external faces continue to move outwards, until the mouths of the tubes are in communication. Because the external faces are joined together and move outward together, the sterile interiors are not exposed to the external faces or the environment. As such, the non-sterile, contaminated external face of the first flange is in contact with only the non-sterile, contaminated external face of the second flange. Thus, the sterile surface of the first tube is only exposed to the sterile surface of the second tube. Thus, when the flexible materials have been fully displaced, the resulting connection connects one sterile tube with another without exposure to contaminated surfaces.

A second aspect of the present disclosure includes two flanges composed of semi-flexible material, each enclosing the distal end of an interiorly sterile tube. Each of the tubes may be any type of closed conduit, and may be composed of any material. The flanges have an external face, which may be covered with a protective film. The films can be removed and the external faces can be attached together. The attachment can be temporary or permanent and can be achieved in any way sufficient to keep the two external faces attached as the sterile connection is created. For example by hook and loop, screws, snaps, welds, clamps, adhesive, magnetic force, pressure, and/or other attachment technique. The tubes are then moved toward one another and the semi-flexible material of the flanges moves radially or axially outward from the tubes. The semi-flexible materials tear, rip, fold bend, buckle, mushroom, melt, crumple, or are otherwise displaced, moving radially and/or axially outward and uncovering the sterile tubes. Similar to the first aspect, the sterile surfaces come into contact with only other sterile surfaces. The sterile surfaces are not exposed to the environment or the contaminated external faces of the flanges. When the displacement is complete the resulting connection is sterile.

A third aspect of the present disclosure includes flanges composed of flexible and non-flexible materials connected to, surrounding, or forming the distal end of an interiorly sterile tube. The flexible portions are respectively connected to a tube and extend from the distal end of the tube outward. For example, four flexible portions may be present, two per tube. For example, the flexible portions may be arranged side-by-side, two per tube, such that they form a seam between the distal end of the tube and an endface. The flexible portions are kept in place by supports. Between the flexible portions and the supports is a semi-flexible pull. For example four semi-flexible pulls may be present, two per tube and each extending from substantially the middle of a respective flange outward. The semi-flexible pulls may be arranged similarly to the flexible portions. When pulled, the semi-flexible pulls transfer a force to the flexible portions. Each flange has an external face that is formed by the flexible portions and covers the mouth of the tube. Protective films cover the external faces of both flanges. The protective coverings can be removed from the external faces, and the external faces can be attached to one another using, for example, hook and loop, screws, snaps, welds, clamps, adhesive, magnetic force, pressure, mechanical fasteners and/or other attachment techniques.

The respective pairs of semi-flexible portions of the flanges, two per tube, are pulled in opposite directions substantially perpendicular to the tubes. The force is transferred through the semi-flexible portions of the flanges to the flexible materials. The supports help maintain the flexible portions in contact with the semi-flexible portions and help maintain the flexible portions of one of the flanges in contact with the flexible portions of the other flange. First the flexible portions move outward and start to open the respective seams adjacent the mouths of the tubes. As the semi-flexible portions are pulled further, the flexible portions that extend perpendicular to the mouths of the tube move radially or axially outward. The flexible portions that extend parallel to the tubes are urged forward. As force continues to be applied, the parallel portions associated with each of the respective tubes move toward one another and then radially or axially outward. As the flexible portions move away from the mouths of the tubes a point or other opening at the adjacent the center of the tubes is opened. The point spreads gradually into a linear opening generally along the seam as the flexible portions continue to be pulled. The opening is sterile because the external faces are attached together. The sterile surfaces are not exposed to the environment or the contaminated external faces of the flanges. When the displacement is complete the resulting connection is sterile.

A fourth aspect of the present disclosure includes a male piece and a female piece. Both pieces surround, form, or are connected to a distal end of an interiorly sterile tube. Both the female piece and the male piece are composed of flexible materials. When the male piece is inserted into the female piece, the male portion fits within a preformed indentation on the surface of the female piece. When force is applied along one of the tubes, movement of the tubes is translated into axial or radial movement of a portion of the of the male piece that correspondingly displaces a portion of the female piece. Due at least in part to the flexible materials of the male and female pieces, portions of them are displaced radially and/or axially outward from the tubes and the sterile interiors of the tubes connect.

A fifth aspect of the present disclosure includes flanges surrounding, forming, or connected to the distal ends of two interiorly sterile tubes. Each flange has an external face that covers the mouth of the enclosed tube. A fluid is disposed in the sterile tubes. The external face of each flange may be exposed to the environment, but the sealed, sterile interiors of the tubes remain uncontaminated because of the fluid. The two flanges are attached temporarily or permanently along their external faces, for example by hook and loop, screws, snaps, welds, clamps, adhesive, magnetic force, pressure, and/or other attachment technique. The fluid is pressurized from within the respective tubes. The fluid in both tubes can be displaced towards the opposite tube and flange. After exiting the mouth of the tubes, the fluid from both flanges moves radially or axially outward, propelled by the pressure gradient created by the opposing flange. That is, the fluid in each of the respective tubes is urged toward the other tube. By suitably balancing the respective pressures, e.g., applying substantially equal pressures, the respective fluid in each tube is urged radially or axially outward. As the fluid continues to be displaced to connect the two sterile interiors of the tubes.

BRIEF DESCRIPTION OF THE DRAWINGS

FIG. 2A is an exemplary schematic representation of a connector apparatus in accordance with the present disclosure;

FIG. 2B is an alternative view of the connector apparatus of FIG. 2A;

FIG. 2C is an alternative view of a flange of the connector apparatus of FIG. 2A;

FIG. 2D is a sectional view of the connector apparatus of FIG. 2A;

FIG. 5 is an exemplary schematic representation of a connector apparatus in accordance with the present disclosure;

FIG. 5A is a sectional view of the connector apparatus of FIG. 5;

DETAILED DESCRIPTION

Figure 1:
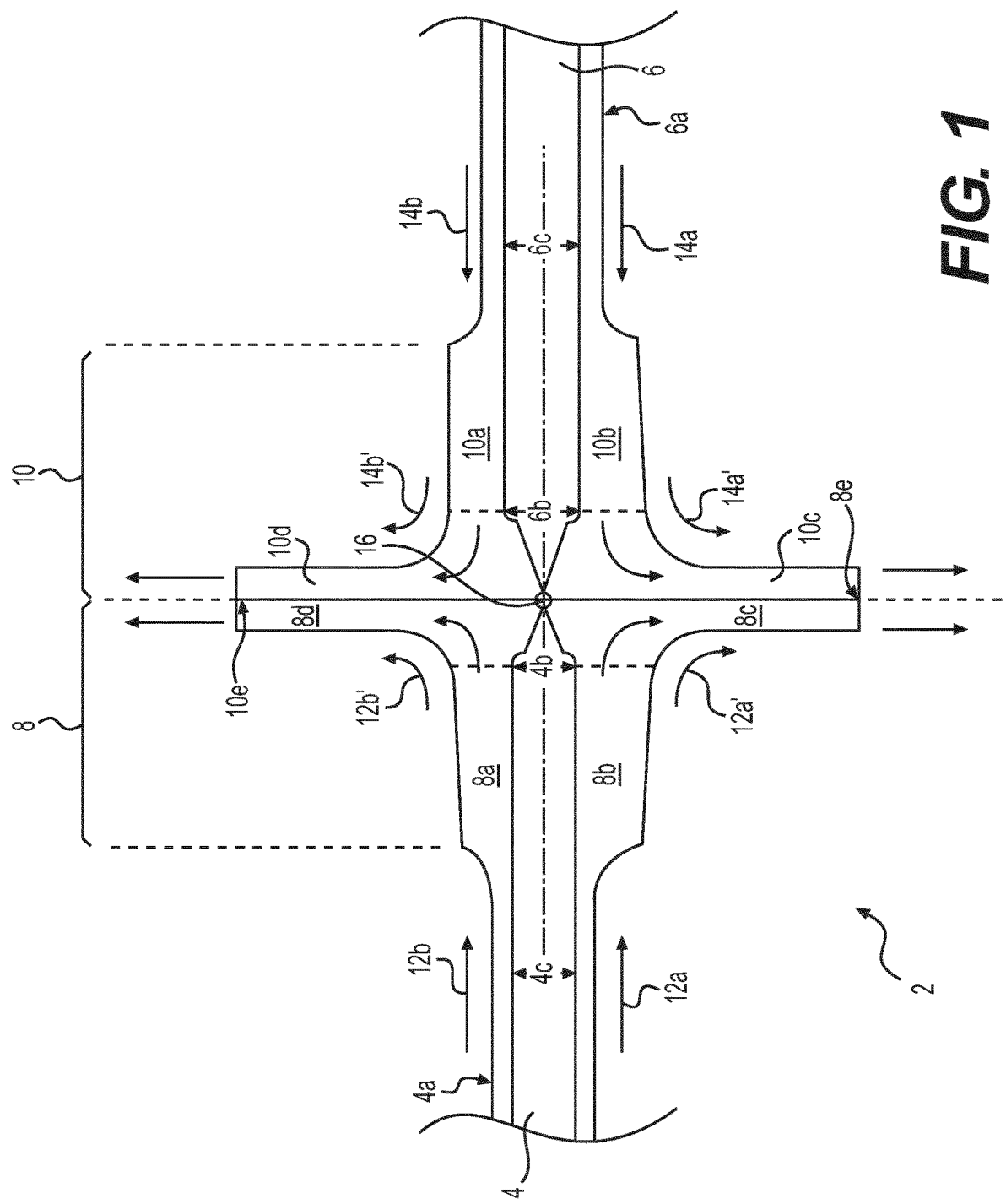
FIG. 1 is an exemplary schematic representation of a connector apparatus in accordance with the present disclosure.

FIG. 1 illustrates a schematic representation of an exemplary connector apparatus 2 in accordance with the present disclosure. Connector apparatus 2 includes two tubes, a first tube 4 and a second tube 6. Each tube respectively includes an external surface, 4a and 6a, a mouth 4b and 6b, and an interior surface 4c and 6c. Tubes 4 and 6 each have distal and proximal ends. The distal end of tube 4 is disposed within, is formed with, or is otherwise included in flange 8. The distal end of tube 6 is disposed within, is formed with, or is otherwise included in flange 10. Both flange 8 and flange 10 are composed of a flexible material. Flanges 8 and 10 include portions of flexible material 8a, 8b, 10a and 10b, surrounding exterior 4a and exterior 6a. Additionally flanges 8 and 10 include portions of flexible material 8c, 8d, 10c and 10d, which are substantially perpendicular, within manufacturing and/or assembly tolerances, to exteriors 4a and 6a and cover mouths 4b and 6b. Flanges 8 and 10 also include external faces 8e and 10e. Portions 8c and 8d form external face 8e. Portions 10c and 10d form external face 10e. Directions 12a, 12a', 12b, 12b', 14a, 14a', 14b, and 14b', are also shown.

Tubes 4 and 6 may be any type of closed conduit, including piping, hoses, and tubes of any size or diameter. It is contemplated that tubes 4 and 6 could be any shape. Tubes 4 and 6 can be of any material suitable for and/or capable of moving fluids, gases, or other products, byproducts, or ingredients depending on the particular system. At their proximal end tubes 4 and 6 may be connected or otherwise in communication with one or more units of a manufacturing or processing system, such as, for example, a product reservoir, manufacturing equipment, or processing equipment. When a connection is made the product moves from, for example, product storage to a mixer. Such a product moves through tubes 4 and 6, flowing along interior surfaces 4c and 6c towards mouths 4b and 6b.

Interior surfaces 4c and 6c are sterile, and mouths 4b and 6b are sealed. Exterior surfaces 4b and 6b may be exposed to a non-sterile environment. But it is contemplated that the present disclosure is also applicable to systems or environments where external surfaces 4b and 6b are also sterile.

Flanges 8 and 10 are composed of a flexible material. The flexible material can be any material that is deformable when force is applied. The material may be configured to tear, rip, fold bend, buckle, mushroom, melt, crumple, or be otherwise displaced from mouths 4b and 6b.

Flange 8 surrounds, forms, or is connected the distal end of tube 4. Flange 8 flares outward from the distal end of tube 4 and covers mouth 4b. Portions 8a and 8b extend parallel to tube 4 from the base of flange 8 to mouth 4b. Portions 8c and 8d are substantially perpendicular to tube 4 and cover mouth 4b. Portions 8c and 8d form external face 8e. External face 8e lies a plane substantially parallel, within manufacturing tolerances, to mouth 4b. External face 8e may be exposed to the environment.

Flange 10 is disposed similarly about tube 6. Flange 10 surrounds, forms, or is connected to the distal end of tube 6. Portions 10a and 10b surround exterior 6a. Portions 10c and 10d cover mouth 6b and form external face 10e. External face 10e lies a plane substantially parallel, within manufacturing tolerances, to mouth 6b. External face 10e may be exposed to the environment.

It is contemplated flanges 8 and 10 might be preformed with tubes 4 and 6 therein. Alternatively flanges 8 and 10 may be separate pieces that are inserted over or snapped onto the distal ends of tubes 4 and 6 when a connection is required. It is also contemplated that flanges 8a, 10a, and in particular, external faces 8e and 10e, may lie in respective plans that extend from or extend relative to the tubes 4, 6 at any angle.

To connect tubes 4 and 6, flange 8 and flange 10 are generally aligned and attached together. External faces 8e and 10e are positioned with portion 8d adjacent to portion 10d, portion 8c adjacent to portion 10c, and mouth 4b substantially centered on mouth 6b, all within manufacturing tolerances. External faces 8e and 10e may be attached by, for example, hook and loop, screws, snaps, welds, clamps, adhesive, magnetic force, pressure, mechanical fasteners and/or other attachment techniques. The attachment can be temporary or permanent.

Once external faces 8e and 10e are attached, force is applied on flange 8, urging it toward flange 10, and on flange 10, urging it toward flange 8. The force applied to flange 8 may be equal to the force applied to flange 10, but it is contemplated that unequal forces may also be applied. The applied force causes flanges 8 and 10 to deform. Portion 8b moves along direction 12a, and portion 8a moves along direction 12b. Substantially simultaneously portion 10b moves along direction 14a, and portion 10a moves along direction 14b. The movement of portions 8a, 8b, 10a, and 10b translates through the rest of flanges 8 and 10. As portions 8a and 10a move toward one another, further movement causes portion 8d to be displaced along direction 12b', and causes portion 10d to be displaced along direction 14b'. Similarly, as portions 8b and 10b move toward one another, portion 8c is displaced outward along direction 12a' and portion 10c is displaced outward along direction 14a'. As flanges 8 and 10 deform they may tear, rip, fold, bend, buckle, mushroom, melt, crumple, or be otherwise displaced.

The displacement of portions 8c, 8d, 10c, and 10d, by portions 8a, 8b, 10a and 10b, causes external faces 8e and 10e to move axially or radially outward. Because external faces 8e and 10e are attached, they move together, spreading outward from mouths 4b and 6b at approximately the same rate.

Tubes 4 and 6, which were originally offset by flanges 8 and 10, move closer to one another, and mouths 4b and 6b are uncovered, exposing sterile interiors 4c and 6c. Sterile interior 4c and sterile interior 6c are uncovered substantially simultaneously as external faces 8e and 10e tear, rip, fold bend, buckle, mushroom, melt, crumple, or are otherwise displaced from mouths 4b and 6b. First point 16 is exposed. External faces 8e and 10e continue to recede from point 16 as flanges 8 and 10 are further displaced. The continued displacement expands point 16 into a larger opening. Because faces 8e and 10e move outward from point 16, and because face 8e is and remains in contact with face 10e, no non-sterile surface or edge crosses point 16 or the resulting opening. Sterile interiors 4c and 6c may then be further uncovered, connecting tubes 4 and 6.

The attachment between 8e and 10e prevents contamination. Face 8e acts as a barrier between mouth 4b and contaminants located on face 10e, and face 10e acts as a barrier between mouth 6b and contaminants located on face 8e. Neither face 8e nor face 10e can contaminate tubes 4 and 6 while faces 8e and 10e are attached.

FIG. 2A illustrates a second schematic representation of an exemplary connector apparatus 17 in accordance with the present disclosure. Apparatus 17 includes a first flange 18 and a second flange 20. Flange 18 surrounds, forms, or is connected to tube 22 and flange 20 surrounds, forms, or is connected to tube 24. Flanges 18 and 20 also have portions of flexible material 18a, 18b, 20a and 20b, with cut 18b' and cut 20b' therein (see FIG. 2D). Flanges 18 and 20 also include semi-flexible support materials 18c and 20c. Support materials 18c and 20c include bands 18c' and 20c' and stays 18c'', 20c'', 18c''', and 20c'''. In addition flange 18 has external face 18d and flange 20 has external face 20d. Tubes 22 and 24 have external surfaces 22a and 24a, mouths 22b and 24b, and interior surfaces 22c and 24c. Apparatus 17 may also include protective films 28 and 30.

As shown in FIG. 2D, tubes 22 and 24 include exterior surfaces 22a and 24a, mouths 22b and 24b, and interior surfaces 22c and 24c. Tubes 22 and 24 can be of any shape, size, or material, as required by the particular application. Both tube 22 and tube 24 have a distal end and a proximal end. The distal ends of tubes 22 and 24 are enveloped by flanges 18 and 20 respectively. In addition tubes 22 and 24 each have a proximal end that may be linked to one or more units of a manufacturing or processing system, such as, for example, a product reservoir, manufacturing equipment, or processing equipment. Exterior surfaces 22a and 24a are the outer surfaces of tubes 22 and 24, and may be exposed to the environment. Inner surface 22c of tube 22 and inner surface 24c of tube 24 are the inner surfaces of tubes 22 and 24. Where a sterile connection is desired inner surfaces 22c and 24c are sterile. Tubes 22 and 24 may be of any material, and may be any type of closed conduit, including piping, hoses, and tubes of any size or diameter. It is contemplated that tubes 22 and 24 could be any shape.

The distal end of tube 22 is disposed within or formed in flange 18 and the distal end of tube 24 is disposed within or formed in flange 20. Flanges 18 and 20 surround exteriors 22a and 24a and cover mouths 22b and 24b, as shown in FIG. 2D.

Flanges 18 and 20 include both flexible material and support structures. The flexible material can be any material that is deformable when force is applied. At least a portion of, or all of, flange 18 or flange 20 may be composed of a material that may tear, rip, fold bend, buckle, mushroom, melt, crumple, or be otherwise displaced when flanges 18 and 20 are pushed together. Portion 18a is disposed along exterior 22a and portion 20a is disposed along exterior 24a. Portion 18b covers mouth 22b, and portion 20b covers mouth 24b. Portions 18a and 18b may be a single piece (as shown in FIG. 2B) or may comprise multiple pieces, likewise portions 20a and 20b may be a single piece or may comprise multiple pieces.

Within both portion 18b and portion 20b there is a small gap, perforation, groove, slice, cut, or other weakened area 18b' and 20b' positioned approximately over the center of mouths 22b and 24b. Cuts 18b' and 20b' extend from mouths 22b and 24b partially through portions 18b and 20b toward external faces 18d and 20d. Cuts 18b' and 20b' may help the flexible material break apart in a predictable way.

Portion 18b forms external face 18d of flange 18, and portion 20b forms external face 20d of flange 20 (as shown in FIG. 2C). External faces 18d and 20d lie in a plane substantially parallel, within manufacturing tolerances, to sealed mouths 22b and 24b respectively, as shown in FIG. 2C. External faces 18d and 20d may be optionally covered by protective films 28 and 30. Films 28 and 30 may also be caps, cushioning or other coverings. External faces 18d and 20d may also be sticky, tacky, or equipped with adhesive, hook and loop, snaps or other devices to aid in connecting flanges 18 and 20.

Flanges 18 and 20 also include support structures 18c and 20c. Support structures 18c and 20c are disposed within and around flexile portions 18a, 18b, 20a, and 20b. Support structures 18c and 20c may be composed of any rigid or semi-flexible material. Support structure 18c has band 18c', and stays or ribs 18c" and 18c'". Support structure 20c has band 20c', and stays or ribs 20c", and 20c'".

As shown in FIG. 2D, band 18c' is a collar, band, or ring, encircling the base of portion 18a, furthest from external face 18d. Similarly, band 20c' encircles the base of portion 20a, furthest from external face 20d. It is contemplated that bands 18c' and 20c' may be permanently attached to flanges 18 and 20 or bands 18c' and 20c' may be formed integrally with flanges 18 and 20. Within flanges 18 and 20 the stays, fingers, or ribs 18c", 18c'", 20c", 20c'" extend from band 18c' or 20c' through portions 18a or 20a and then generally extend radially or axially outward along portions 18b or 20b. Stays 20c" and 20c'" and stays and 18c" and 18c'" are shown in FIG. 2D. Stays 20c" and 20c'" are connected to band 20c' and stays 18c" and 18c'" are connected to band 18c'. Though only two stays or ribs are visible in each of flange 18 and flange 20 it is contemplated that one or more additional stays or ribs could be included. For example, each flange may include 1, 2, 3, 4, 5, 6, or more stays or ribs. Stays 18c" and 18c'" and stays 20c" and 20c'" may be uniformly or non-uniformly spaced. Stays 18c" and 18c'" may be positioned to align with stays or ribs 20c" and 20c'" when external face 18d and external face 20d are attached, or stays 18c" and 18c'" may be offset from stays or ribs 20c" and 20c'". It is contemplated that instead of stays, full trumpets of semi-rigid material might extend through flanges 18 and 20 from bands 18c' or 20c'. It is also contemplated that the respective bands or collars may completely or partially surround a respective tube.

When a connection is made protective films 28 or 30, are removed and flanges 18 and 20 are aligned so that external face 18d is substantially covered by external face 20d and cut 18b' is substantially aligned with cut 20b'. External face 18d is attached to external face 20d to generally maintain the alignment of 18b' and 20b' at least while the connection is made. The external faces 18d and 20d may be attached by any combination of hook and loop, screws, snaps, welds, clamps, adhesive, magnetic force, pressure, mechanical fasteners and/or other attachment technique. The attachment may be temporary or permanent, and may involve multiple attachment techniques.

Once external faces 18d and 20d are attached, force is applied to bands 18c' and 20c', moving bands 18c' and 20c' toward one another. Bands 18c' and 20c' may be moved manually or automatically. The force applied to band 18c' may be equal to the force applied to band 20c', but it is contemplated that unequal forces may also be applied. As bands 18c' and 20c' are urged toward one another along the axis of tubes 22 and 24 cuts 18b' and 20b' tear, rip, fold bend, buckle, mushroom, melt, crumple, or are otherwise displaced in the direction of faces 18d and 20d. The movement of bands 18c' and 20c' also translates through stays 18c" and 18c'" and 20c" and 20c'". Stays 18c" and 18c'" and 20c" and 20c'" continue to the outer edges portions 18b and 20b. As stays 18c" and 18c'" and 20c" and 20c'" are urged forward, the outer ends of the stays, contained in portions 18b and 20b are moved outward from the axis of tubes 22 and 24. The movement forward and out of 18c" and 18c'" and 20c" and 20c'" causes portions 18b and 20b to move outward as well. Portions 18b and 20b split along cuts 18b' and 20b' and move radially and/or axially outward from the center of mouths 22b and 24b. As portions 18b and 20b move, their flexible material may tear, rip, fold bend, buckle, mushroom, melt, crumple, or be otherwise displaced.

As force continues to be applied to bands 18c' and 20c', portions 18a and 20a are also forced radially and/or axially outward, generally following the path previously taken by portions 18b and 20b.

The deformation of flanges 18 and 20 also forces external faces 18d and 20d radially and/or axially outward, moving interiors 22c and 24c closer together. As 18d and 20d continue to be displaced, interiors 22c and 24c are uncovered. First a point at the center of mouths 22b and 24b is exposed. The point gradually spreads into an opening as more of external faces 18d and 20d are displaced. Both the point and the opening are sterile because face 18d and face 20d are attached together and therefore unable to contaminate interiors 22c and 24c as mouths 22b and 24b are uncovered because all of the non-sterile surface of external face 18d is covered by the non-sterile surface of external face 20d, and vice versa. Once external faces 18d and 20d have been displaced, exposing mouth 22b to mouth 24b to the desired degree, the sterile connection is complete.

Figure 3A:
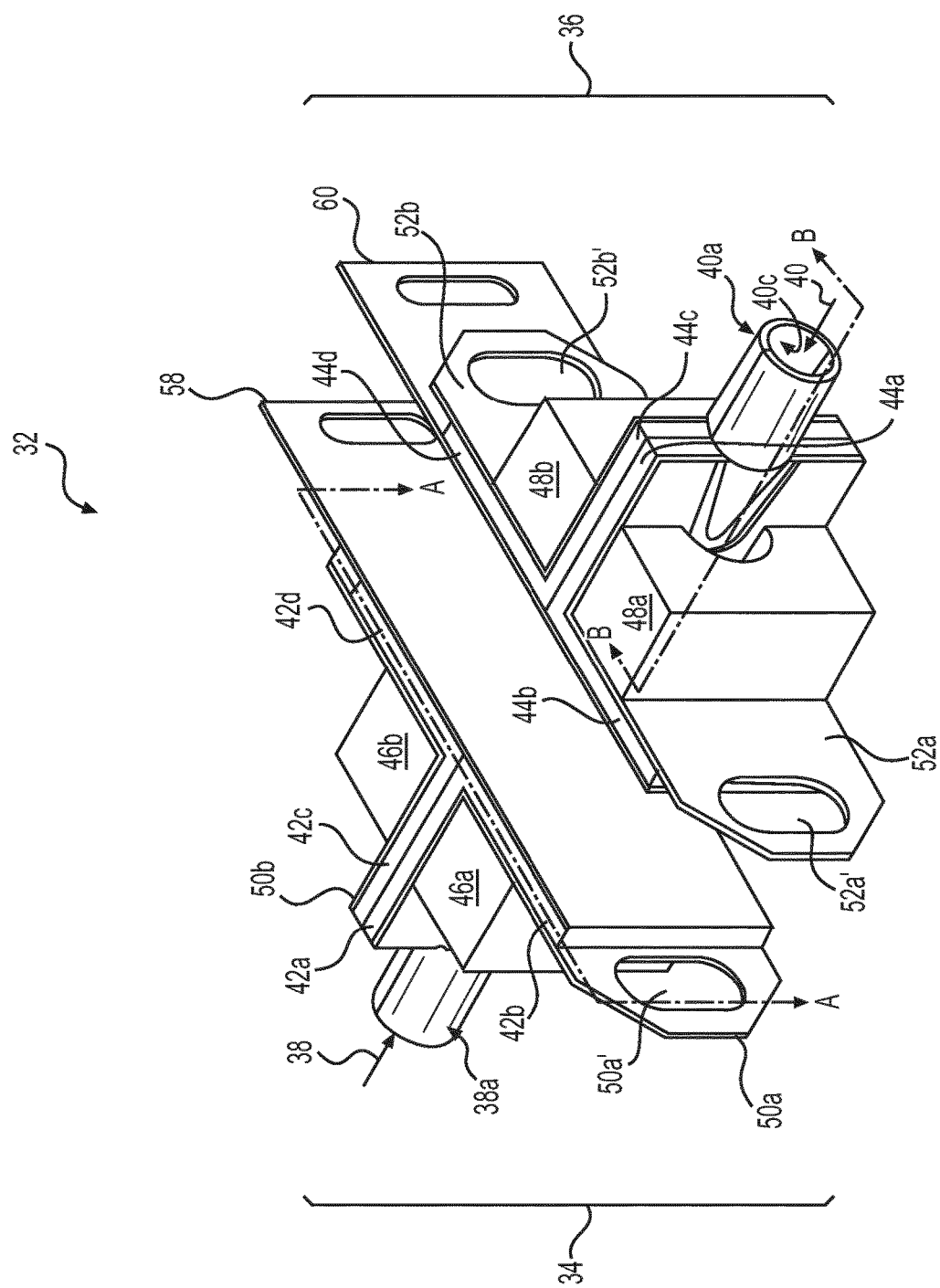
FIG. 3A is an exemplary schematic representation of a connector apparatus in accordance with the present disclosure.

FIG. 3A illustrates a third schematic representation of an exemplary connector apparatus 32 in accordance with the present disclosure. Apparatus 32 includes flanges 34 and 36. Each contains or includes a tube 38 or 40. Tubes 38 and 40 each have exteriors 38a and 40a, mouths 38b and 40b, and sterile interiors 38c and 40c (as illustrated in FIG. 3C). Flange 34 includes portions of flexible material 42a, 42b, 42c, and 42d, as well as supports 46a and 46b. Flange 36 includes portions of flexible materials 44a, 44b, 44c, and 44d and supports 48a and 48b. Flanges 34 and 36 also include pulls. Flange 34 includes pulls 50a and 50b. Flange 36 includes pulls 52a and 52b. Pull 50a has handle 50a', pull 50b has handle 50b', pull 52a has handle 52a', and pull 52b has handle 52b'. Flange 34 has external face 54 and Flange 36 has external face 56. External faces 54 and 56 may be protected by a film 58 or 60.

Tubes 38 and 40 include non-sterile exterior surfaces 38a and 40a, mouths 38b and 40b, and sterile interiors 38c and 40c. Tubes 38 and 40 may be linked at their proximal ends to one or more units of a manufacturing or processing system. Such units may include, for example, a product reservoir, manufacturing equipment, or processing equipment. Tubes 38 and 40 may be any type of closed conduit, including piping, hoses, and tubes of any size or diameter. Tubes 38 and 40 can be any shape, size or material, depending on the particular application.

Both flange 34 and flange 36 are composed of portions of flexible materials 42 and 44. Flange 34 has an external face 54 and flange 36 has external face 56. Flange 34 surrounds, forms, or is connected to the distal end of tube 38. Flange 36 surrounds, forms, or is connected to the distal end of tube 40. It is contemplated that tubes 38 and 40 may or may not be centered in flanges 34 and 36.

Figure 3B:
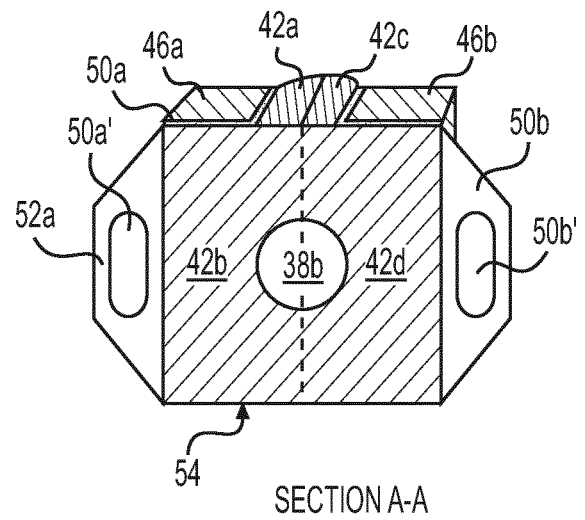
FIG. 3B is a sectional view of the connector apparatus of FIG. 3.
Figure 3C:
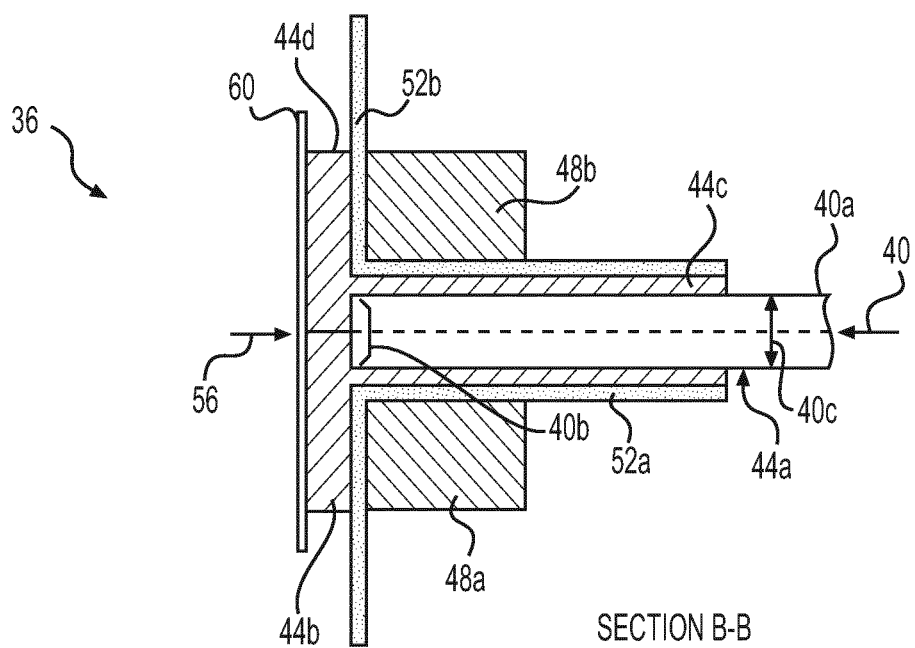
FIG. 3C is a sectional view of a flange of the connector apparatus of FIG. 3.

With reference to flange 34, together portions 42a and 42c surround exterior 38a, as shown in FIG. 3B. Portions 42a and 42c are disposed substantially parallel to tube 38, within manufacturing tolerances. Portions 42a and 42c end at mouth 38b and merge into or connect with portions 42b and 42d respectively. Portions 42b and 42d are disposed substantially perpendicular to mouth 38b, within manufacturing tolerances, and meet substantially at the center of mouth 38b and, for example, form a seam. Together portions 42b and 42d cover mouth 38b, and form external face 54 of flange 34.

The flexible portions of flange 36 are similarly positioned, as shown in FIG. 3C. Portion 44a and portion 44c run substantially parallel to tube 40 surrounding exterior 40a, within manufacturing tolerances. At mouth 40b portion 44a merges into or connects with portion 44b, which runs substantially perpendicular to mouth 40b, within manufacturing tolerances. Correspondingly, 44c merges into or connects with portion 44d, which runs substantially perpendicular, within manufacturing tolerances, to mouth 40b. Portions 44b and 44d meet at the center of mouth 40b and, for example, form a seam. Together portions 44b and 44d cover mouth 40b and form external face 56 of flange 36.

It is contemplated that portions 42a and 42b can be made from an integral piece of flexible material, portions 42c and 42d can be made from a second integral piece of flexible material, portions 44a and 44b can be made from a third integral piece of flexible material, and portions 44c and 44d can be made from a fourth integral piece of flexible material. As depicted portions 42a and 42b, portions 42c and 42d, portions 44a and 44b, and portions 44c and 44d each form a right angle, but it is contemplated that flexible materials 42 and 44 might form any other angle, or any curve, e.g., may be radiused, form a conical section, or any other suitable shape.

A support is disposed within each angled grouping of flexible material—e.g., portions 42a and 42b, portions 42c and 42d, portions 44a and 44b, and portions 44c and 44d. Support 46a is positioned against portions 42a and 42b, support 46b is positioned against portions 42c and 42d, support 48a is positioned against portions 44a and 44b, and support 46b is positioned against portions 44c and 44d. Depicted as blocks, supports 46a, 46b, 48a, and 48b, can be any shape and need not be solid. It is contemplated that braces, magnets, capsules or other containers of pressurized air or other tension-providing apparatus can also be used to help maintain portions 42 and 44 in place and in contact when forming a connection. Supports 46a, 46b, 48a, and 48b do not necessarily extend the whole length of flexible materials 42 and 44, although it is contemplated that they can. Supports 46a, 46b, 48a, and 48b may also help maintain portions 42 and 44 in position around tubes 38 and 40.

Disposed between each pair of respective portions 42a and 42b, 42c and 42d, 44a and 44b, and 44c and 44d, and the corresponding support 46a, 46b, 48a, and 48b, is a pull. Pull 50a is disposed between support 46a and portions 42a and 42b. Pull 50a extends along the entire length of portions 42a and 42b, and may extend past the outwardly extending edge of 42b. Pull 50b is disposed in a similar position with respect to portions 42c and 42d, and is disposed between support 46b and portions 42c and 42d. Pulls 52a and 52b are disposed similarly in flange 34. Pull 52a is disposed between portions 44a and 44b and support 48a, and pull 52b is positioned between portions 44c and 44d and support 48b. Pulls 50a, 50b, 52a, and 52b may include handles, 50a', 50b', 52a', and 52b', respectively, which extend past the edge or edges of external faces 54 and 56 and allow force to be applied to pulls 50a, 50b, 52a, and 52b. In addition or alternatively pulls 50a, 50b, 52a, and 52b might contain tabs, loops, strings, or other actuation devices.

External faces 54 and 56 may be protected by films 58 and 60. Alternatively, external faces 54 and 56 may be protected by caps, cushioning, or other coverings, or films 58 and 60 may be omitted entirely. External faces 54 and 56 may also be equipped with adhesive, snaps, magnets, threading, hook and loop, ties, or other attachment tools to facilitate the attachment of flanges 34 and 36.

To connect tubes 38 and 40, protective films 58 and 60 are first removed. Flanges 34 and 36 and are then aligned so that external face 54 substantially covers external face 56 and vice versa, and so the center of tube 38 substantially aligns with the center of tube 40, within manufacturing tolerances. Flange 34 is then attached to flange 36. The attachment can be either temporary or permanent and can be facilitated with one or more attachment tools, such as hook and loop, screws, snaps, welds, clamps, adhesive, magnetic force, pressure, mechanical fasteners and/or other attachment technique suitable for substantially maintaining the connection between external faces 54 and 56.

Once faces 54 and 56 are attached, force is applied to pulls 50a, 50b, 52a, and 52b. Force may be applied manually or automatically. Pulls 50a and 52a are pulled substantially simultaneously away from tubes 38 and 40 as pulls 50b and 52b are pulled substantially simultaneously in the opposite direction, away from tubes 38 and 40. The force applied to pulls 50a and 52a may be equal to the force applied to pulls 50b and 52b, but it is contemplated that unequal forces may also be applied. Similarly, the force applied to pulls 50a and 50b may be equal to the force applied to pulls 52a and 52b, but it is contemplated that unequal forces may also be applied. Because pulls 50a, 50b, 52a, and 52b are disposed between flexible materials 42 and 44 and supports 46a, 46b, 48a, and 48b, the force applied to pulls 50a, 50b, 52a, and 52b is transferred to the flexible materials 42 and 44. Portion 42b, is pulled outward with portion 44b, as portions 42d and 44d are pulled outward in the opposite direction.

The radial or axial movement of portions 42b, 44b, 42d, and 44d causes portion 42a to move towards portion 44a as portion 44a is pulled toward portion 42a. Substantially simultaneously, portions 42c and 44c are pulled towards one another. Portions 42a, 44a, 42c, and 44c thus move toward external faces 54 and 56 and then follow portions 42b, 44b, 42d, and 44d, respectively, outward. Portions 42 and 44 may tear, rip, fold, bend, buckle, mushroom, melt, crumple, or be otherwise displaced as they move radially and/or axially outward away from tubes 38 and 40. Throughout movement, supports 46 and 48 maintain tension on portions 42a, 44a, 42c, 44c, 42b, 44b, 42d, and 44d and help maintain faces 54 and 56 together.

As flexible materials 42 and 44 move, external faces 54 and 56 are displaced. The displacement of external faces 54 and 56 moves tubes 38 and 40 closer together. As the displacement of external faces 54 and 56 continues, mouths 38b and 40b are gradually exposed, first at a point at the center of tubes 38 and 40. The point expands into an opening as faces 54 and 56 continue to move. Both the point and the opening are sterile because external faces 54 and 56 are attached together and therefore unable to contaminate interiors 38c and 40c as mouths 38b and 40b are uncovered because all of the non-sterile surface of external face 54 is covered by the non-sterile surface of external face 56, and vice versa. Once external faces 54 and 56 have been displaced, exposing mouth 38b to mouth 40b to the desired degree, the sterile connection is complete.

Figure 4:
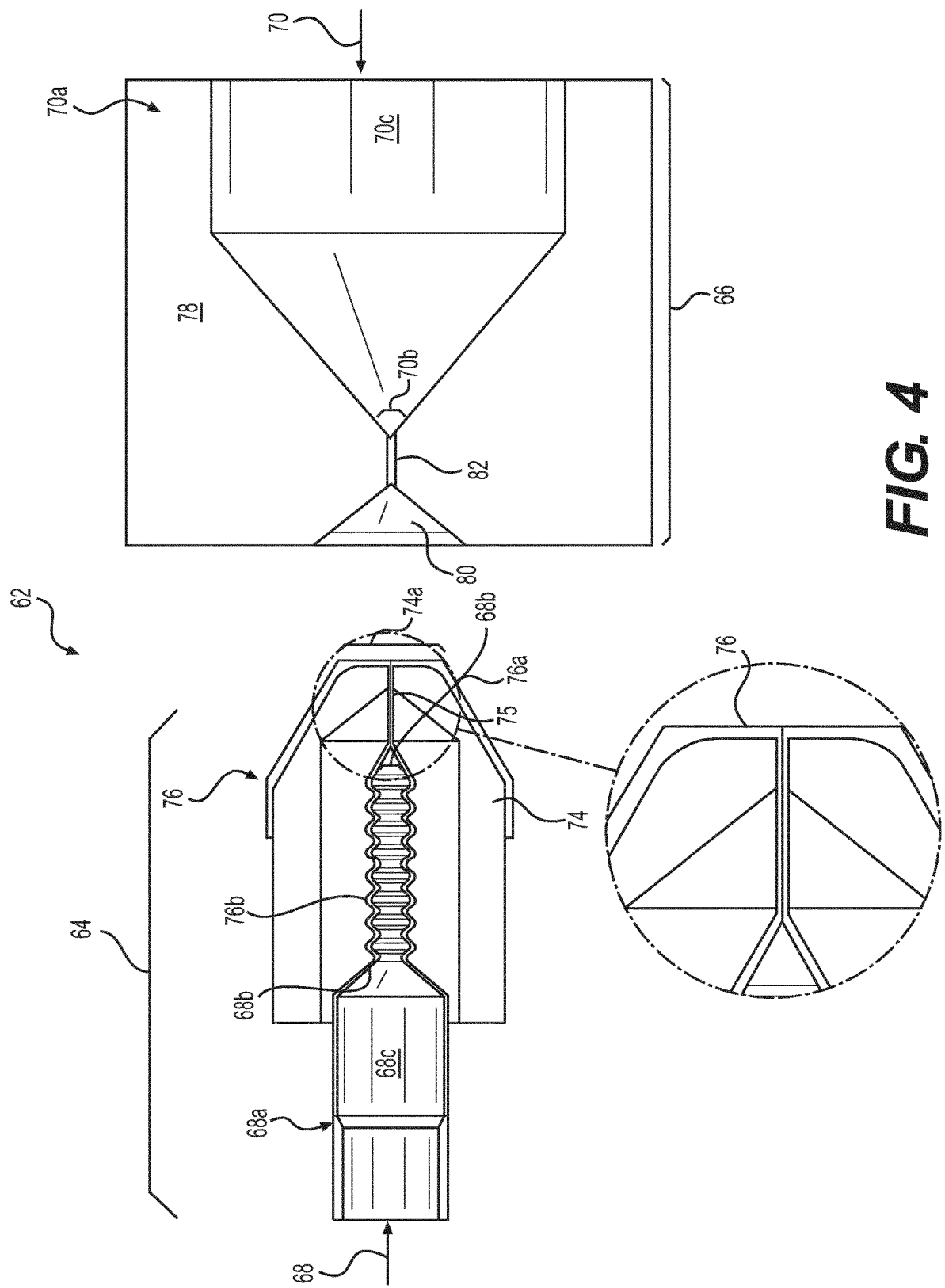
FIG. 4 is an exemplary schematic representation of a connector apparatus in accordance with the present disclosure.

FIG. 4 illustrates a fourth schematic representation of an exemplary connector apparatus 62 in accordance with the present disclosure. Apparatus 62 includes male piece 64 and female piece 66. Male piece 64 surrounds, forms, or is connected to the distal end of tube 68. Similarly, female piece 66 surrounds, forms, or is connected to the distal end of tube 70. Tubes 68 and 70 include exteriors 68a and 70a, sealed mouths 68b and 70b, and sterile interiors 68c and 70c. Male piece 64 includes flexible portion 74, and sheet 76, which is composed of portions 76a and 76b. Flexible portion 74 of the male piece 64 contains a flaw, break, or thin spot 75. Female piece 66 is composed of flexible portion 78 and includes indentation an 80, with a flaw, break, or thin spot 82. Both pieces 64 and 66 may have protective films covering some or all of the flexible portions. Tubes 68 and 70 may be any material or shape, and may be any type of closed conduit. Both tube 68 and tube 70 have distal and proximal ends. Each of tubes 68 and 70 may be linked at their proximal end to one or more units of a manufacturing or processing system. Such units may include, for example, a product reservoir, manufacturing equipment, or processing equipment.

Male piece 64 includes flexible portion 74, and pull 76. Tube 68 is disposed within flexible portion 74. Flexible portion 74 envelopes mouth 68b and has front outer edge 74a which lies a plane substantially parallel to mouth 68b. It is contemplated that flexible portion 74 may taper conically or pyramidally into front outer edge 74a, but male piece may be any shape. Front outer edge 74a may also be of any shape, for instance front outer edge 74a may be pointed, flat, rounded, or concave. Within flexible portion 74 is a flaw, slit, or thin spot 75. It is contemplated that slit 75 may be a tear, cut, break, divot, perforation or other weakening element. Flexible portion 74 may be formed from an integral piece, and may be made from any material that is displaced when tube 68 moves through it, such as a rubber, a foam, a gel, or any other flexible or semi-flexible material.

Surrounding tube 68, between exterior 68a and flexible portion 74, is sheet 76. Sheet 76 begins at the base of flexible portion 74, where it meets tube 68. It is contemplated however that sheet 76 may begin at another point. Sheet 76 includes portions 76a and 76b that together envelop or cover the distal end of tube 68. At mouth 68b. Portions 76a and 76b come into contact and extend parallel to one another from mouth 68b through slit 75 in flexible portion 74. Portions 76a and 76b extend front outer edge 74a and diverge outward from slit 75, such that each covers a portion of front outer edge 74a, and together portions 76a and 76b cover all of front outer edge 74a.

Female piece 66 is composed of flexible portion 78, which envelopes the distal end of tube 70, covering mouth 70b. Flexible portion 78 may be composed of any material that can be displaced by male piece 64. Flexible portion 78 may form any shape around tube 70, for example a block or a sphere. Flexible portion 78 contains a flaw, break, or thin spot 82. Flaw 82 is disposed substantially in line with the center of mouth 70b. It is contemplated that flaw 82 may be a tear, cut, break, divot, perforation or other weakening element.

Flexible portion 78 also includes an indentation, cavity, dent, depression, or pit 80. Indentation 80 is generally formed in the outer surface of flexible material 74. Indentation 80 is substantially aligned, within manufacturing tolerances, with both flaw 82 and mouth 70b. Indentation 80 is sized to accommodate front outer edge 74a. Protective films may be placed over pull 74b and over indentation 80. It is contemplated that caps, cushioning, or other coverings may be substituted.

To connect tubes 68 and 70 the protective films, if present, are removed. Front outer edge 74a of male piece 64 is then pushed or placed into indentation 80 of female piece 66. Front outer edge 74a and indentation 80 are then attached. The attachment between front outer edge 74a and indentation 80 may be accomplished using hook and loop, screws, snaps, welds, clamps, adhesive, magnetic force, pressure, mechanical fasteners and/or other attachment techniques suitable for substantially maintaining an attachment between front outer edge 74a and indentation 80. The attachment between front outer edge 74a and indentation 80 generally aligns tubes 68 and 70. Sheet 76 is disposed between front outer edge 74a and indentation 80. It is contemplated that sheet 76 may adhere to indentation 80.

Tube 68 is then moved toward tube 70. The force on tube 68 may be generated manually or automatically. Tube 70 may likewise be moved toward tube 68 or held stationary. As tube 68 moves forward it presses into flexible portion 74, displacing front outer edge 74a. As force continues to be applied to tube 68, front outer edge 74a is gradually opened at slit 75 and flexible portion 74 is displaced radially outward from slit 75. Because front outer edge 74a is enveloped by indentation 80, the displacement of flexible portion 74 causes flexible material 78 to be displaced in turn. Flexible material 80 breaks at flaw 82 and is moved radially outward from flaw 82 as tube 68 continues to displace flexible portion 74.

Sheet 76 is disposed between front outer edge 74a and indentation 80. The displacement of flexible materials 74 and 78 pulls sheet 76 radially outward, away from mouth 68b, and creates tension on sheet 76, which is affixed to exterior 68a below mouth 68b. This tension generates a force on tube 68. The tension on sheet 76 causes tube 68 to move deeper into flexible material 74. As sheet 76 is pulled away from tube 68, portions 76a and 76b diverge and are pulled radially outward with flexible materials 74 and 78.

The further movement of tube 68 continues to displace flexible portions 74 and 78. As flexible portions 74 and 78 continue to be displaced, the movement of front outer edge 74a and indentation 80 pulls sheet 76 away from tube 68, and creates tension on sheet 76. The movement of tube 68 further displaces flexible portions 74 and 78. As flexible portions 74 and 78 move away from tubes 68 and 70 they may tear, rip, fold bend, buckle, mushroom, melt, crumple, or be otherwise displaced.

Mouth 68b is gradually brought into contact with mouth 70b. Because front outer edge 74a and indentation 80 are attached while the connection is made, neither can contaminate mouth 68b or mouth 70b—front outer edge 74a acts as a barrier, protecting mouth 68b from indentation 80, and indentation 80 acts as a barrier protecting mouth 70b from front outer edge 74a. Front outer edge 74a and indentation 80 move together as flexible portions 74 and 78 are displaced, thus mouth 68b is drawn into a sterile point which opens into a sterile plane as tube 68 is drawn forward and flexible portions 74 and 78 continue to be displaced. When flexible portions 74 and 78 are displaced from mouth 70b to the desired degree, and mouth 68b has been pulled into contact with the exposed portion of mouth 70b, the connection is complete.

FIG. 5 illustrates a fifth schematic representation of an exemplary connector apparatus 84 in accordance with the present disclosure. Connector apparatus 84 includes a first tube 86 and a second tube 88. Each tube includes an external surface, 86a and 88a, a mouth 86b and 88b, and an interior surface 86c and 88c. Flange 90 surrounds, forms, or is connected to tube 86 and flange 92 surrounds, forms, or is connected to tube 88. Flange 90 has external face 90a and flange 92 has external face 92a. External faces 90a and 92a each have a flaw, break, or thin spot 102 or 104. Within flange 90 is chamber, pocket, or hollow space 94. Contained within chamber 94 is substance 95. Similarly, within flange 92 is chamber, pocket, or hollow 96 containing substance 97. A sheet or film of fluid, foam, or flexible gel 98 may be disposed over external face 90a. A similar sheet or film fluid, foam, or flexible gel 100 may be disposed over external face 92a. Substances 95 and 97 and gels 98 and 100 may be the same substance, may each be different substances, and/or may include any combination of the same and different substances.

Both tube 86 and tube 88 have a distal end and a proximal end. At their proximal ends tubes 86 and 88 may be linked to one or more units of a manufacturing or processing system. Such units may include, for example, a product reservoir, manufacturing equipment, or processing equipment. At their distal end, tubes 86 and 88 are each capped by a flange.

Figure 5C:
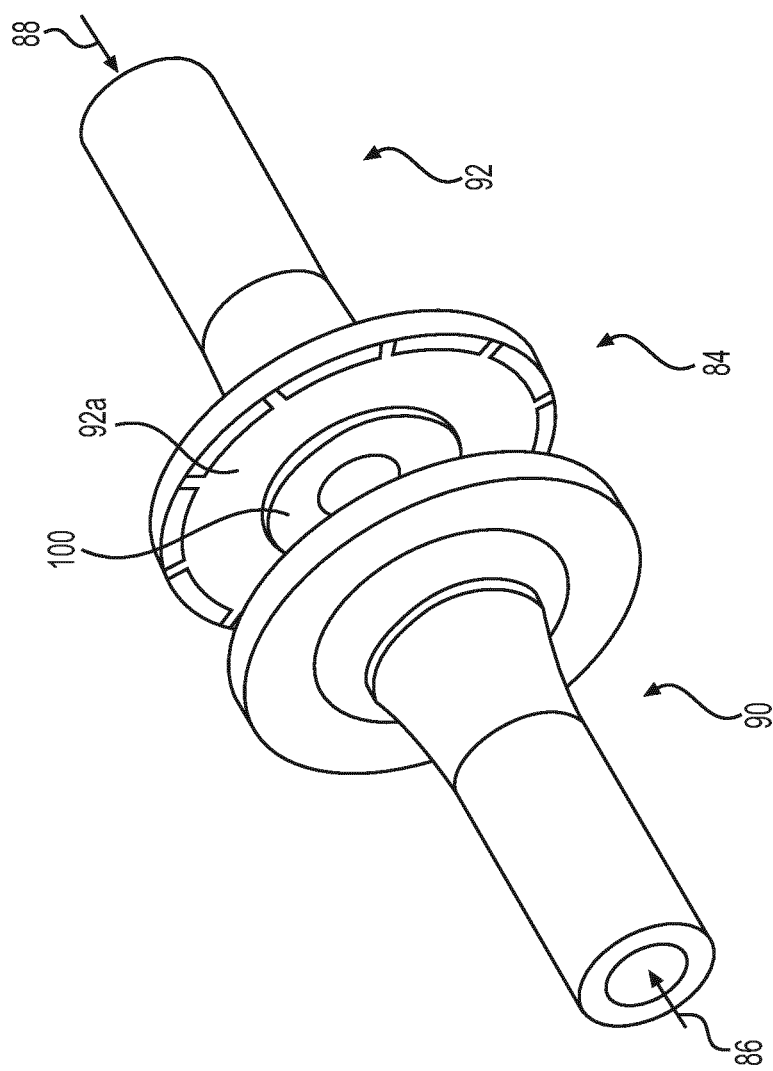
FIG. 5C is an alternative view of the connector apparatus of FIG. 5.
Figure 5B:
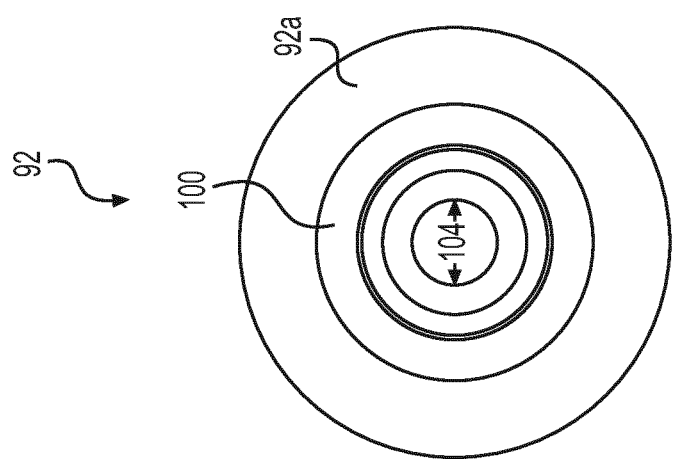
FIG. 5B is an alternative view of a flange of the connector apparatus of FIG. 5.

Flange 90 envelops the distal end of tube 86, as shown in FIG. 5A. Flange 90 flares radially or axially outward from exterior 86a to envelop mouth 86b. Flange 90 may be composed of a semi-flexible or rigid material. Flange 90 has an external face 90a, which covers mouth 86b, forming a plane substantially perpendicular, within manufacturing tolerances, to the path of tube 86. External face 90a has a thin spot 102 substantially aligned with the center of mouth 86b, within manufacturing tolerances. Flange 92 is similarly configured, as shown in FIG. 5C. Flange 92 envelops the distal end of tube 88. Flange 92 flares radially or axially outward from exterior 88a to envelop mouth 88b. Like flange 90, flange 92 may be composed of a semi-flexible or rigid material. Flange 92 has an external face 92a, which covers mouth 88b, forming a plane substantially perpendicular to the path of tube 88, within manufacturing tolerances, as shown in FIG. 5B. Thin spot 102 in external face 92a is disposed in line with the center of mouth 88b, within manufacturing tolerances. Gel 100 is disposed on external face 92a. Between external face 92a and mouth 88b is chamber 96.

Flanges 90 and 92 may be preformed with tubes 86 and 88 or may be separate pieces that are inserted over or snapped onto the distal ends of tubes 86 and 88 when a connection is required. Gels 98 and 100 may be any substance that will spread or flow when force is applied. It is contemplated that the properties of gels 98 and 100 may vary by temperature, by pressure, or when magnetized, allowing control over whether gels 98 or 100 are generally firm or spreadable. It is also contemplated that gel 98 and gel 100 may be different substances. It is further contemplated that gel 98 and/or gel 100 may be composed of semi-flexible or inflexible materials that react to the material of the opposing gel, to cause one or both to become flexible or inflexible.

Chambers 94 and 96 contain substances 95 and 97. Substances 95 and 97 may contain the same fluid, foam, or gel used for gels 98 and 100, or a different fluid or gas. It is contemplated that substances 95 and 97 may be different. Chamber 94 is disposed between external face 90a and mouth 86b. At mouth 86b chamber 94 connects to tube 86 and has substantially similar dimensions, within manufacturing tolerances. Chamber 94 extends from mouth 86b toward external face 90a, and includes or is disposed immediately adjacent to thin spot 102. Chamber 96 is similarly positioned. Chamber 96 extends from mouth 88b toward external face 92a, and includes or is immediately adjacent to thin spot 104.

Thin spots 102 and 104 are provided in exterior faces 90a and 92a. It is contemplated that thin spots 102 and 104 might be tears, cuts, breaks, divots, perforations or other weakening elements. External faces 90a and 92a, including gels 98 and 100, may be covered with protective films, caps, cushioning, and/or other coverings. External faces 90a and 92a may also be equipped with adhesive, snaps, magnets, threading, hook and loop, ties, or other attachment tools to facilitate an attachment between external face 90a and external face 92a.

To connect tubes 86 and 88, any protective films are first removed from external faces 90a and 92a. External faces 90a and 92a are then attached such that external face 90a substantially covers external face 92a and thin spots 102 and 104 are substantially aligned, within manufacturing or assembly tolerances. The attachment between external faces 90a and 92a may be temporary or permanent, and may be accomplished using hook and loop, screws, snaps, welds, clamps, adhesive, magnetic force, pressure, mechanical fasteners and/or other attachment techniques suitable for substantially maintaining an attachment between external faces 90a and 92a. The attachment of faces 90a and 92a merges or attaches gels 98 and 100.

Once external faces 90a and 92a are attached, substances 95 and 97 are pressurized. Substances 95 and 97 can be pressurized by heating substances 95 and 97, by pinching tubes 86 and 88 to decrease the volume of chambers 94 and 96, or by using an external device, for example a clamp, to apply pressure to substances 95 and 97. Substances 95 and 97 may also be pressurized by using a separate device to force a sterile substance through or to inject a sterile substance into tubes 86 and 88 to create pressure on substances 95 and 97, for example by allowing products or air to flow into the proximal ends of tubes 86 and 88.

Pressure builds up in chambers 94 and 96. Eventually, substance 95 reaches its maximum pressure and breaks through external face 90a and gel 98 at thin spot 102. Similarly, substance 97 is brought to its maximum pressure and breaks through external face 92a and gel 100 at thin spot 104. Substance 95 and substance 97 displace gel 98 and gel 100 as they emerge through thin spots 102 and 104. The continued application of pressure on chambers 94 and 96 forces the remaining substance 95 and the remaining substance 97 out of chambers 94 and 96 through thin spots 102 and 104. Substance 95 and substance 97 are pushed radially and/or axially outward by the pressure gradient created by the application of pressure to chambers 94 and 96. The movement of substance 95 and substance 97 also urges gels 98 and 100 radially outward. As substance 95 and substance 97 displace gel 98 and gel 100 from external faces 90a and 92a, chambers 94 and 96 are gradually exposed to one another. Because tube 86 connects to chamber 94 and 88 connects to chamber 96 the exposure of chamber 94 to chamber 96 allows a connection between tubes 86 and 88.

The connection created between tube 86 and tube 88 is sterile. Of the materials forming the barrier between tube 86 and tube 88 only gels 98 and 100 are ever exposed to the environment. Gels 98 and 100 merge or are attached together when external faces 90*a* and 92*a* are attached. The attachment between gel 98 and gel 100 provides that the contaminated surface of gel 98 and the contaminated surface of gel 100 move together—gel 98 acts as a barrier, preventing contaminants found on gel 100 from contacting interior 86*c*. Similarly, gel 100 acts as a barrier between the contaminants found on the surface of gel 98 and the interior 88*c*. As a result, when substances 95 and 97 come into contact, their connection is sterile. When substance 95 and substance 97 have pushed gel 98 and gel 100 fully away from the thin spots 102 and 104, product flowing through tube 86 has a sterile path with which to reach tube 88.

Those skilled in the art will recognize various modifications and variations can be made to the present disclosure. Other embodiments will be apparent to those skilled in the art from consideration of the disclosures made here. It is intended that the specification and examples be considered as exemplary only.

We claim:

1. A connection apparatus comprising:
a first tube and a second tube, each tube having an external surface, a mouth, and an interior surface;
first and second flanges respectively surrounding, forming, or connecting with the first and second tubes, each flange having:
an external face;
a flaw, break, or thin spot; and
a chamber, pocket, or hollow space within a respective flange;
a first liquid, fluid, gel or foam disposed within the chamber, pocket, or hollow space of the first tube; and
a second liquid, fluid, gel or foam disposed within the chamber, pocket, or hollow space of the second tube;
wherein each flange is configured such that movement of the first tube toward the second tube displaces the first or second liquid, fluid, gel, or foam radially outward with respect to the first and second tubes, and exposure of respective chambers, pockets, or hollow spaces of the first and second tubes to each other forms a connection between the first and second tubes;
wherein a sheet or film of fluid, foam, or flexible gel is disposed over the external face of the first flange and the external face of the second flange;
wherein, when the external face of the first flange is attached to the external face of the second flange, the external face of the first flange substantially covers the external face of the second flange, and the flaw, break, or thin spot of the first flange and the flaw, break, or thin spot of the second flange are substantially aligned;
wherein, when a pressure of the first and second liquid, fluid, gel or foam exceeds a predetermined pressure, the first and second liquid, fluid, gel or foam extends through the sheet or film of fluid, foam, or flexible gel disposed over the respective external faces at the respective flaw, break, or thin spot, and
wherein movement of the first or second liquid, fluid, gel, or foam radially outward with respect to the first and second tubes displaces the sheet or film of fluid, foam, or flexible gel from the external face of the first flange and the external face of the second flange, exposing the chamber, pocket, or hollow space of the first flange to the chamber, pocket, or hollow space of the second flange.

* * * * *